United States Patent
Griffin et al.

(10) Patent No.: US 12,059,508 B2
(45) Date of Patent: Aug. 13, 2024

(54) AUTOMATED SYSTEM AND METHODS FOR TISSUE DEMINERALIZATION

(71) Applicant: ALLOSOURCE, Centennial, CO (US)

(72) Inventors: Aidan Griffin, Denver, CO (US); Timothy Bennett, Denver, CO (US); Joslynn Shamis, Denver, CO (US); Luke Shubin, Denver, CO (US); Yurid Gourgel, Denver, CO (US); Lauren Blume, Denver, CO (US); Kenneth Blood, Denver, CO (US); Adrian Samaniego, Denver, CO (US); Bruce Mock, Denver, CO (US); Cathleen Lucine Badillo, Littleton, CO (US); Matthew Peterson, Denver, CO (US); Reginald Stilwell, Parker, CO (US)

(73) Assignee: Allosource, Centennial, CO (US)

( * ) Notice: Subject to any disclaimer, the term of this patent is extended or adjusted under 35 U.S.C. 154(b) by 1041 days.

(21) Appl. No.: 16/416,654

(22) Filed: May 20, 2019

(65) Prior Publication Data

US 2019/0351102 A1  Nov. 21, 2019

Related U.S. Application Data

(60) Provisional application No. 62/673,439, filed on May 18, 2018.

(51) Int. Cl.
*B01F 27/808*  (2022.01)
*A61L 27/36*  (2006.01)
(Continued)

(52) U.S. Cl.
CPC ....... *A61L 27/3691* (2013.01); *A61L 27/3608* (2013.01); *B01F 27/115* (2022.01);
(Continued)

(58) Field of Classification Search
CPC ............. A61L 27/3691; A61L 27/3608; A61L 27/3687; A61L 2300/414; A61L 2430/34;
(Continued)

(56) References Cited

U.S. PATENT DOCUMENTS 5,275,954 A * 1/1994 Wolfinbarger ...... A61L 27/3691
530/424
7,314,718 B1 * 1/2008 Dasgupta .......... B01L 3/502776
435/7.1
(Continued)

FOREIGN PATENT DOCUMENTS

CN  105169481 A * 12/2015

OTHER PUBLICATIONS

Gilpin, et al. "Decellularization Strategies for Regenerative Medicine: From Processing Techniques to Applications", Biomed Research International, vol. 2017, 13 pages (2017).

*Primary Examiner* — Matthew D Krcha
*Assistant Examiner* — Sophia Y Lyle
(74) *Attorney, Agent, or Firm* — James A. Sheridan; Sheridan Law, LLC

(57) ABSTRACT

Systems and methods for the automated demineralization of bone and decellularization of soft tissue include a mixing assembly communicatively coupled with a control and reporting system. The mixing assembly includes a housing that supports a cannister sub-assembly forming a mixing chamber having a reagent inlet, a reagent outlet, and an internal fluid agitator. A motor is operably coupled with the agitator and configured to spin the agitator in first and second directions relative to the cannister, thereby agitating fluid contained within the mixing chamber. At least one pump is configured to progressively inject measured quantities of a plurality of reagents into the mixing chamber. The associated control and reporting system includes a user terminal that displays a graphical user interface enabling a (Continued)

user to initiate an automated demineralization or decellularization procedure in which the mixing assembly demineralizes tissue placed within the mixing chamber. Other embodiments are also disclosed.

12 Claims, 12 Drawing Sheets

(51) Int. Cl.
  *B01F 27/115* (2022.01)
  *B01F 35/71* (2022.01)
(52) U.S. Cl.
  CPC .......... *B01F 27/808* (2022.01); *B01F 35/714* (2022.01); *A61L 27/3687* (2013.01); *A61L 2300/414* (2013.01); *A61L 2430/34* (2013.01); *A61L 2430/40* (2013.01)
(58) Field of Classification Search
  CPC ............. A61L 2430/40; A61L 2430/02; B01F 27/115; B01F 27/808; B01F 35/714
  See application file for complete search history.

(56) References Cited

U.S. PATENT DOCUMENTS

| | | | | |
|---|---|---|---|---|
| 2009/0215110 A1* | 8/2009 | Gibson | .................. | G01N 21/77 |
| | | | | 435/288.7 |
| 2012/0080118 A1* | 4/2012 | Klein | ...................... | A61L 2/186 |
| | | | | 141/98 |
| 2013/0276842 A1* | 10/2013 | Zajdowicz | ............ | A61L 2/0011 |
| | | | | 134/184 |

\* cited by examiner

AUTOMATED SYSTEM AND METHODS FOR TISSUE DEMINERALIZATION

REFERENCE TO PRIOR PATENT APPLICATION

This application claims the benefit under 35 U.S.C. 119 (e) of U.S. Provisional Patent Application No. 62/673,439, filed May 18, 2018 by Aidan Griffin, Tim Bennett, Joslynn Shamis, Luke Shubin, Yurid Gourgel, Lauren Blume, Kenneth Blood, Adrian Samaniego, Bruce Mock, and Matthew Peterson for "AUTOMATED SYSTEM AND METHODS FOR TISSUE DEMINERALIZATION," all of which patent application is hereby incorporated herein by reference.

BACKGROUND

An allograft includes bone, tendon, skin, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from donor-derived, living-related, or living-unrelated donors and can help patients regain mobility, restore function, enjoy a better quality of life, and even save lives in the case of cardiovascular tissue or skin.

Demineralized bone matrix (DBM) is allograft bone that has had the inorganic mineral removed, leaving behind the organic "collagen" matrix. Removal of the bone mineral exposes more biologically active bone morphogenetic proteins. These growth factors modulate the differentiation of progenitor cells into osteoprogenitor cells, which are responsible for bone and cartilage formation. As a result of the demineralization process, DBM is more biologically active than undemineralized bone grafts. DBM has superior biological properties to undemineralized allograft bone, as the removal of the mineral increases the osteoinductivity of the graft. There are a range of DBM products approved by the Food and Drug Administration for clinical use.

Currently, demineralization procedures for bone and decellularization procedures for other types of soft tissue are accomplished by an operator who mixes tissue to be demineralized/decellularized with several different reagents (e.g., hydrochloric acid, water, phosphate buffered saline) over a progression of separate mixing times. The process is time consuming and, given the number of timed mixing cycles to be completed, the process is not reliably repeatable by human operators. Thus, existing systems and methods for demineralization present time, efficiency, reliability, and quality challenges.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides an automated tissue processing system. The automated tissue processing system may include a mixing assembly, including: (1) a cannister forming a mixing chamber, a reagent inlet configured to convey a liquid into the mixing chamber, and a reagent outlet configured to drain the liquid from the mixing chamber; (2) an agitator disposed within the mixing chamber; (3) a motor operably coupled with the agitator, the motor configured to selectively revolve the agitator in a first direction and in a second direction relative to the cannister; and (4) at least one pump configured to inject a measured quantity of each of a first, a second, and a third reagent into the reagent inlet. The system may also include a control and reporting system in communication with the mixing assembly, the control and reporting system including: (1) a data storage storing a processing module and a reporting module; (2) a processor executing the processing and the reporting modules; and (3) a graphical user interface implemented by the processor and displayed upon a user terminal, the graphical user interface having a number of interactive and preconfigured screens that enable a user to control the mixing assembly to complete an automated demineralization or decellularization process upon a tissue portion placed within the mixing chamber.

Another embodiment provides a system for automatically demineralizing or decellularizing a tissue portion, comprising a control and reporting system in communication with a mixing assembly having a stationary cannister forming an interior mixing chamber configured to receive the tissue portion, a reagent inlet in fluid communication between a plurality of reagent liquid containers and the interior mixing chamber, a reagent outlet in fluid communication between the interior mixing chamber and a waste container, and an agitator rotatively mounted within the interior mixing chamber. The control and reporting system includes a processor communicatively coupled with a data storage storing a processing module, the processor executing the processing module for: (1) inputting a measured quantity of reagent into the interior mixing chamber via the reagent inlet; (2) rotating the agitator within the interior mixing chamber in a first direction relative to the stationary cannister; (3) rotating the agitator within the interior mixing chamber in a second direction relative to the stationary cannister; and (4) draining the measured quantity of the reagent from the interior mixing chamber via the reagent outlet.

Yet another embodiment provides a method of demineralizing a portion of human tissue using an automated mixing assembly controlled via a control and reporting system in communication with the automated mixing assembly. The automated mixing assembly may include a hollow cannister forming a mixing chamber, a reagent inlet in fluid communication with the mixing chamber, a reagent outlet in fluid communication with the mixing chamber, and an agitator rotationally mounted within the mixing chamber. The method may include the steps of: (1) loading the portion of the human tissue into the mixing chamber; and (2) using a graphical user interface (GUI) displayed by the control and reporting system, initiating an automated demineralization procedure at the mixing assembly, the automated demineralization procedure comprising: (a) inputting a measured quantity of a first reagent into the mixing chamber via the reagent inlet; (b) rotating the agitator in a first direction for a first time period; (c) rotating the agitator in a second direction for a second time period; (d) repeating the rotating the agitator in the first and the second directions for a timed mixing cycle period; and (e) draining the measured quantity of the first reagent from the mixing chamber via the reagent outlet.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to the demineralization and/or decellularization of allograft tissue, including bone, soft tissue, and other appropriate types of allograft tissue. More specifically, disclosed embodiments provide an automated system and associated methods of use for demineralizing bone and other tissue portions in a manner that is time-efficient, consistently repeatable, and that allows for quality control and monitoring. Using embodiments of the disclosed system, an operator may place a tissue portion within a mixing chamber of the system, and then program the system for a demineralization or decellularization process, initiate the process, and leave the system unattended while the system carries out the process from initiation to finish, including progressively and independently injecting a plurality of reagents into the mixing chamber, mixing each of the reagents, and draining each of the reagents until demineralization is complete. As discussed above in the Background section, existing demineralization and decellularization mechanisms and techniques fail to provide an automated tissue-processing alternative, which may be programmed as necessary to change demineralization and/or decellularization cycle parameters.

Embodiments of an automated system for tissue demineralization disclosed herein are primarily described in terms of demineralizing bone portions. However, it should be noted that system embodiments may be used in relation to any type of tissue portions that benefit from demineralization such as, for example, skin, tendon, or any other appropriate soft tissue. The system may also be implemented to automate any other appropriate tissue processing procedure, such as, for example, a skin decellularization procedure.

Figure 1:
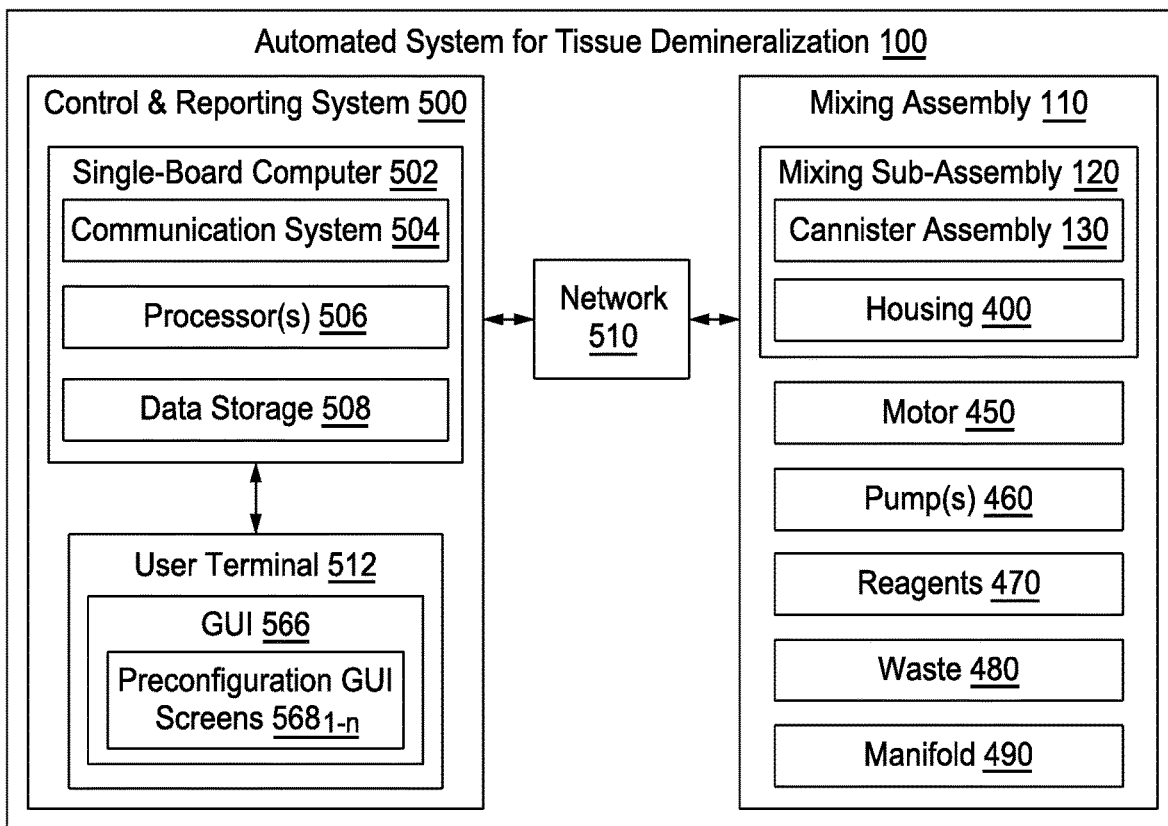
FIG. 1 provides a functional block diagram of one embodiment of an automated system for tissue demineralization.

Turning to the figures, FIG. 1 provides a block diagram of an illustrative system in which various techniques described herein may be implemented according to some embodiments. As shown, one embodiment of an automated system for tissue demineralization 100 may include a mixing assembly 110 that is communicatively coupled with a control and reporting system 500.

In some embodiments, the mixing assembly 110 may include a variety of components configured for the progressive and timed mixing of a plurality of reagents with a bone portion to be demineralized. For example, as schematically represented in FIG. 1 and illustrated in FIG. 2, embodiments of the mixing assembly 110 may include a mixing sub-assembly 120 including an embodiment of a cannister assembly 130 mounted within a stabilizing housing 400 that enables agitation of fluid contained within the cannister assembly 130.

Figure 2:
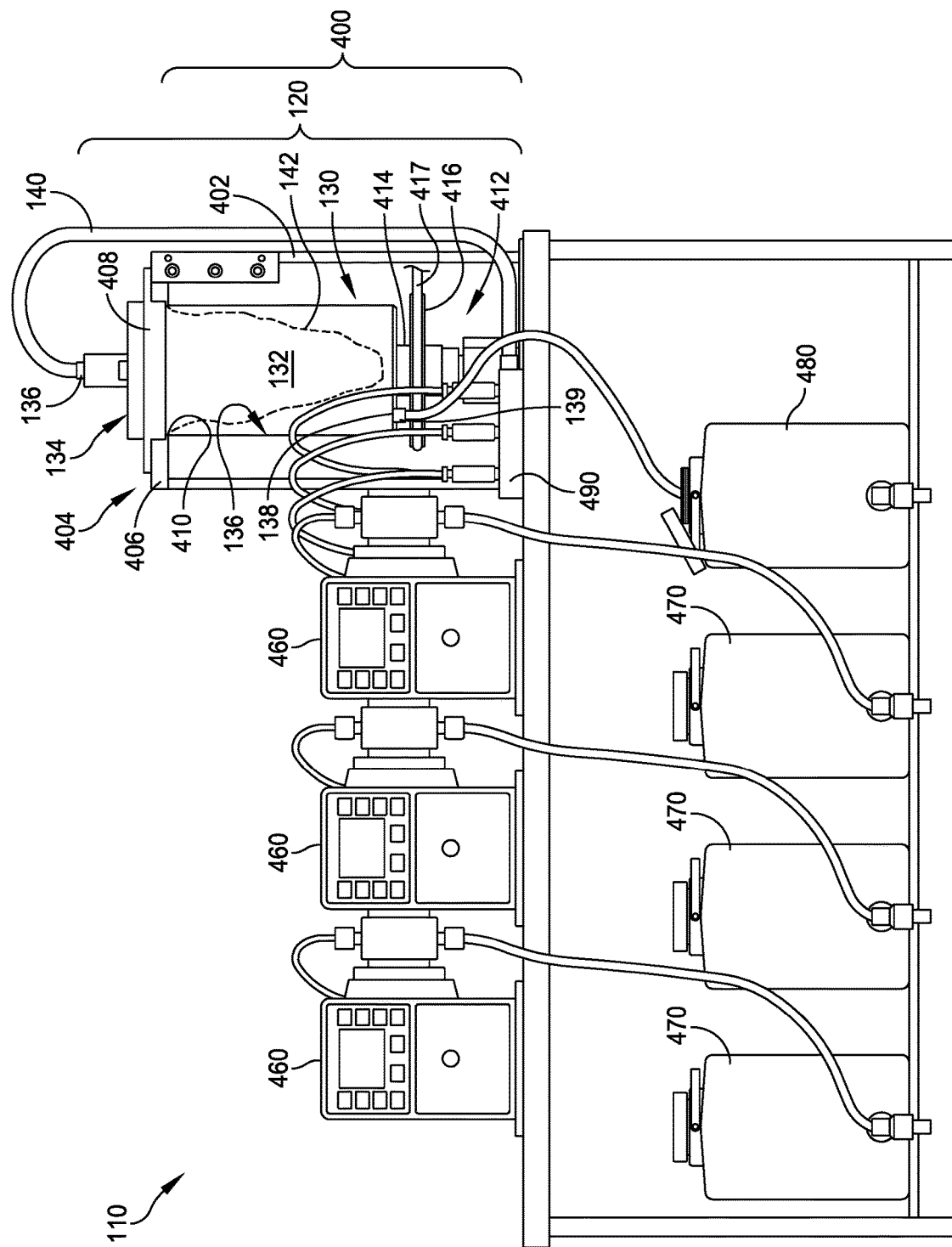
FIG. 2 illustrates a perspective view of one embodiment of a mixing assembly of the automated system for tissue demineralization of FIG. 1.

In one embodiment, the cannister assembly 130 may rotate relative to the stabilizing housing 400 to agitate reagent fluid contained within a hollow canister body 132 forming a mixing chamber 136 therein. In this embodiment, and as shown in FIG. 2, the mixing sub-assembly 120 may include the cannister assembly 130 and the stabilizing housing 400 having a support frame 402 that is fitted at a top end 404 with a bearing holder 406 and corresponding ball bearings 408. The bearing holder 406 may include a recessed aperture 410 configured to receive a top of the cannister assembly 130 such that the cannister assembly 130 may spin freely relative to the bearing holder 406 and the support frame 402.

A bottom end 412 of the support frame 402 may support a rotating base 414 configured to receive a bottom of the cannister 132. The base 414 may incorporate a machined key that ensures proper orientation of the cannister 132 when positioned upon the base 414. In this embodiment, the machined key may be disposed above a wheel 416 that is fitted with a belt 417, which, in turn, is driven by the motor 450 (FIG. 1). To facilitate rotation, the wheel 416 may be attached about a smaller central bearing structure (not shown), resulting in two points of rotation of and support for the cannister body 132—one adjacent to both the top and the bottom of the cannister assembly 130.

The cannister assembly 130 may include a cover 134 and a reagent inlet 136 located at the top of the cannister body 132 and a reagent outlet 138 located at the bottom of the cannister body 132. Both the reagent inlet 136 and the reagent outlet 138 may be fitted with rotary unions that allow the mixing chamber to rotate independently of any connected tubing 140. The reagent outlet 138 allows reagents to drain from the bottom of the mixing chamber 136 to a waste container 480 via gravity when an associated pinch valve is opened.

In one embodiment, the mixing chamber 136 may be fitted with a porous receptacle such as a mesh bag 142 therein to prevent any ground bone or soft tissue fragments from exiting the cannister 132 during the drainage process. In another embodiment, the reagent outlet 138 may be fitted with a pH meter 139, such that the reagent passing through the outlet 138 flows over the pH meter, which checks the pH level of the exiting reagent at the end of the mixing process/ cycle. If the pH level registers too low, the system 100 may repeat the rinse cycles until the pH rises to an acceptable level.

As shown in FIG. 2, some embodiments of the mixing assembly may also include a manifold 490 and one or more pumps 460 that are disposed between the inlet 136 to the hollow cannister body 132 and a plurality of reagent containers 470, each containing a particular reagent (e.g., NaOH, HCl, NaHCO$_3$, Microcyn, PBS, water, and hydrogen peroxide) to be cycled for mixing with the bone portion within the mixing chamber 136. While FIG. 2 shows three reagent containers 470, any appropriate number of reagents may be coupled with the pump(s) 460. In one embodiment, a separate pump 460 may be provided for each reagent (e.g., Watson Marlow Qdos 120), as shown in FIG. 2. In other embodiments, a single multichannel pump or, alternatively, a single pump connected to all of the reagents via a second manifold and using pinch valves to control proper reagent release, may be employed to reduce the footprint of the mixing assembly 110.

FIGS. 3A-3D illustrate perspective, exploded, side, and cross-sectional views of another embodiment of a cannister assembly 230 for incorporation into the mixing sub-assembly 120. In this embodiment, the reagent agitation is initiated from within the cannister for more effective and precise agitation in which the reagent liquid is stirred or agitated with a multi-directional, rotating internal agitator within the stationary outer cannister body.

In this embodiment, the cannister assembly 230 may include a cannister chamber body 232 and a drainable base 234 that combine to form a mixing chamber 236 therein. The drainable base 234 may include a reagent outlet 248 for draining the reagent from the mixing chamber 236 into the waste container 480, as well as a rotation access protrusion 240 configured to receive a rotation translation assembly 250 designed to translate a rotational movement input from the motor 450 (FIG. 1) to an agitator 246 that is rotationally coupled to the rotation translation assembly 250 near the bottom of the mixing chamber 236 via an appropriate fastener 252 such as, for example, a screw. Embodiments of the agitator 246 may include a plurality of upwardly extending protrusions and/or physical anomalies to increase the agitation efficacy of the agitator 246.

Figure 3A:
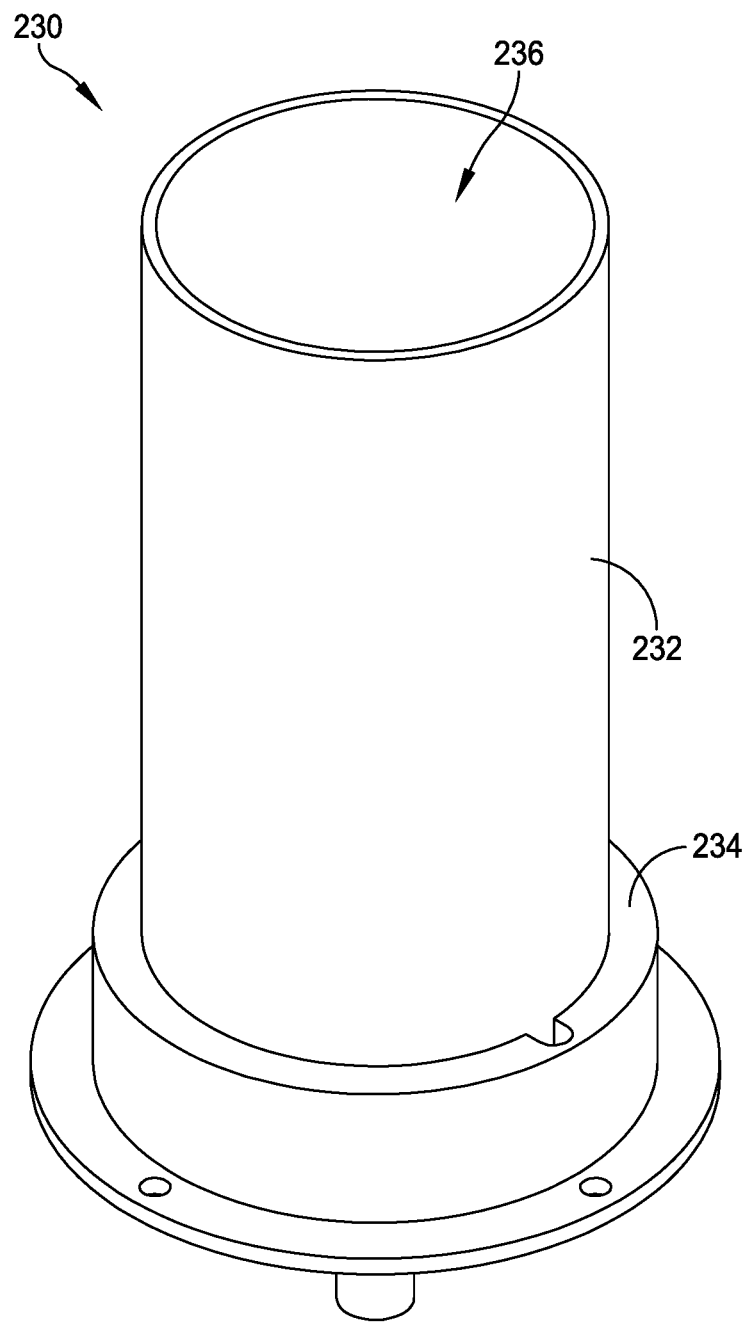
FIGS. 3A-3D illustrate perspective, exploded, side, and cross-sectional views of one embodiment of a cannister assembly for incorporation into the mixing assembly of FIG. 2.
Figure 3B:
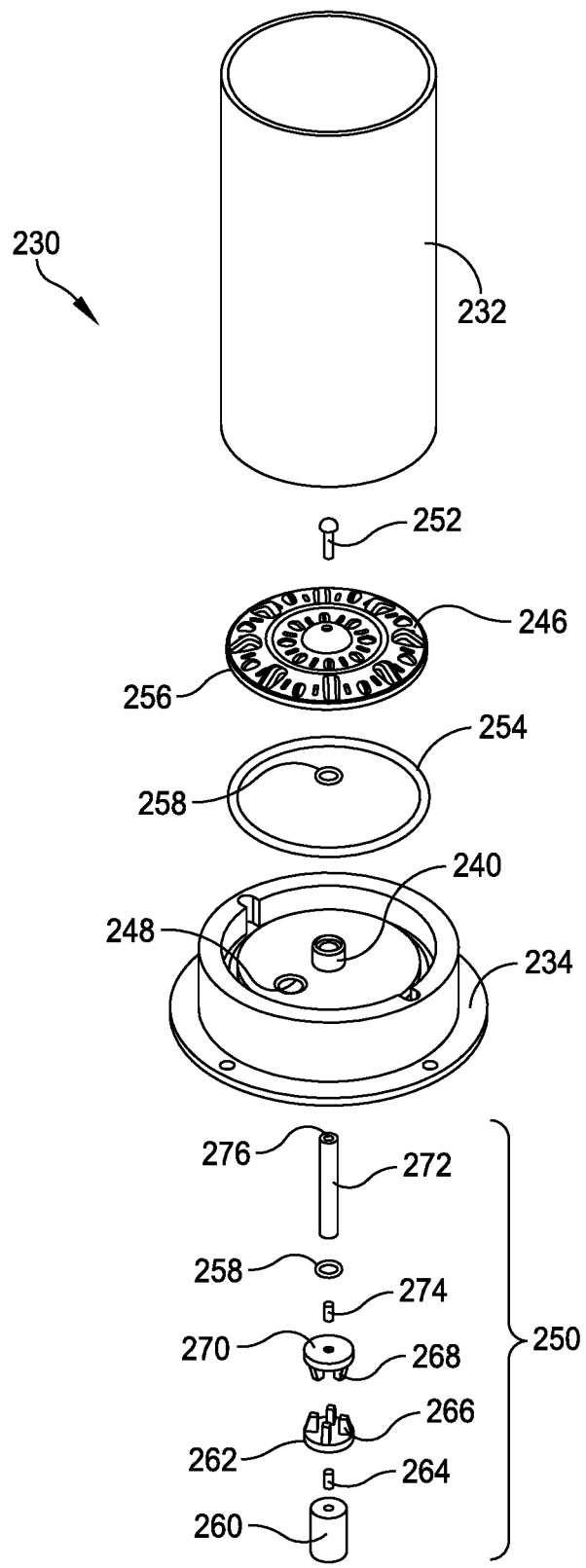
Figure 3C:
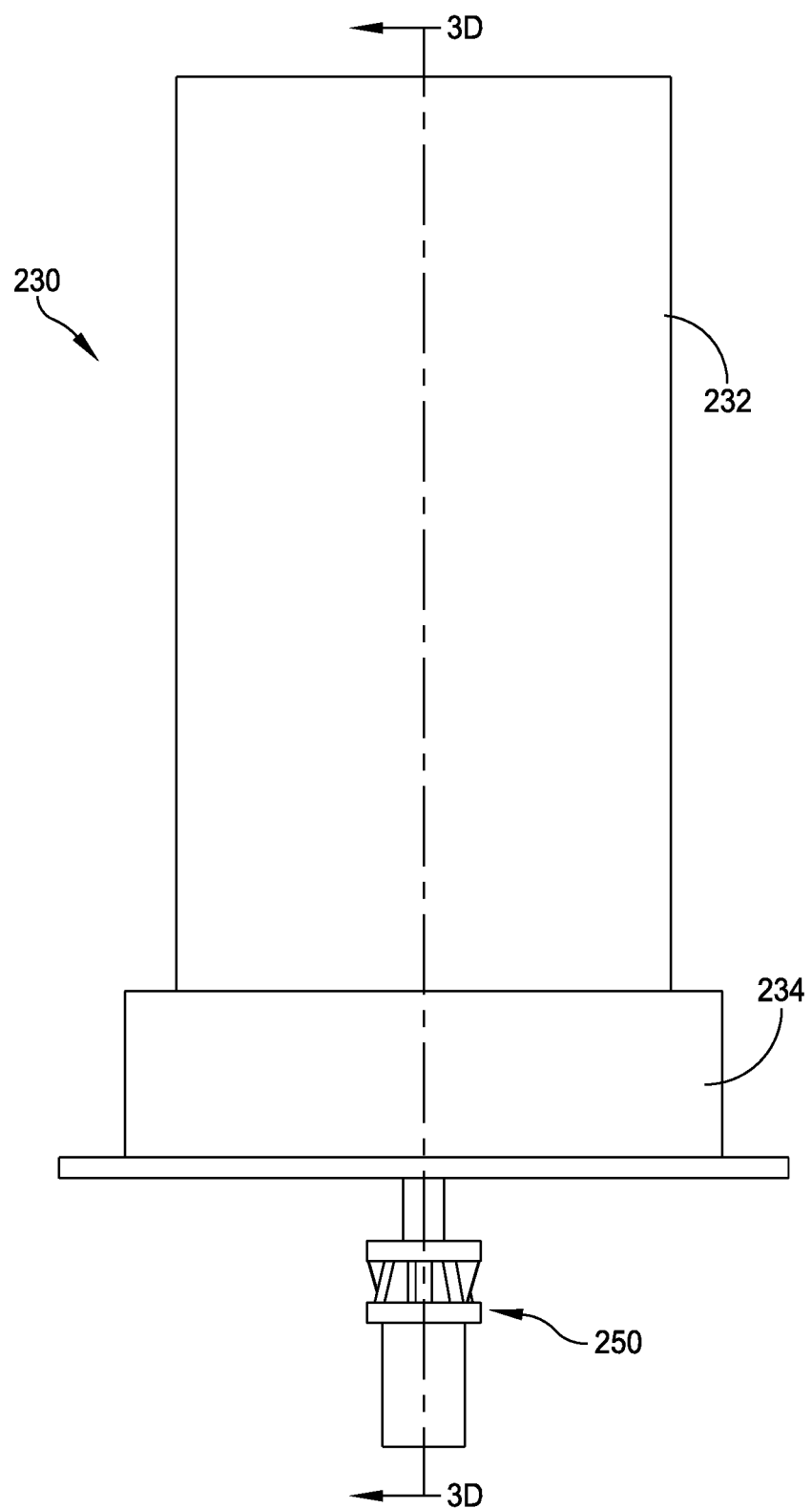
Figure 3D:
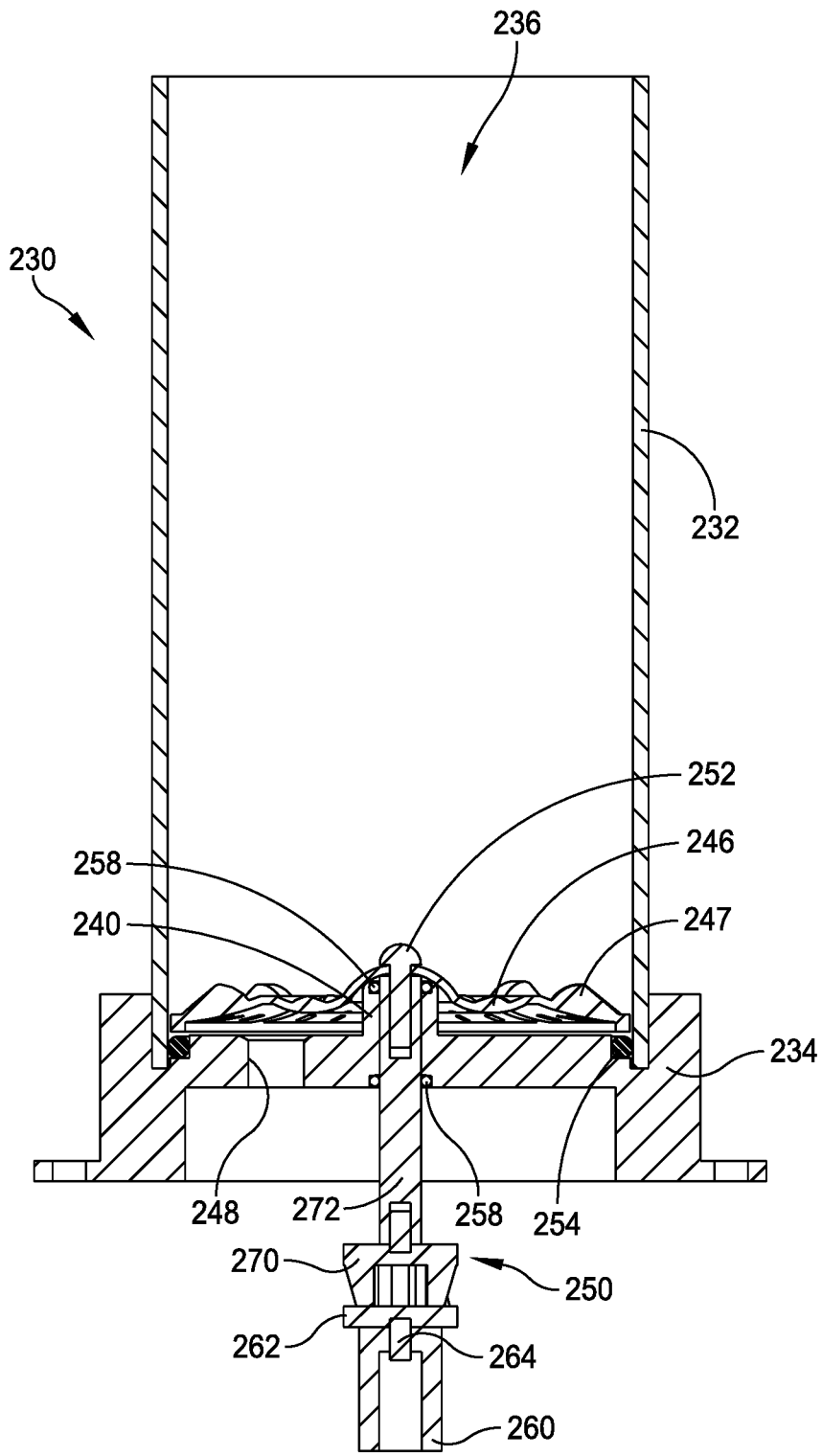
Figure 4A:
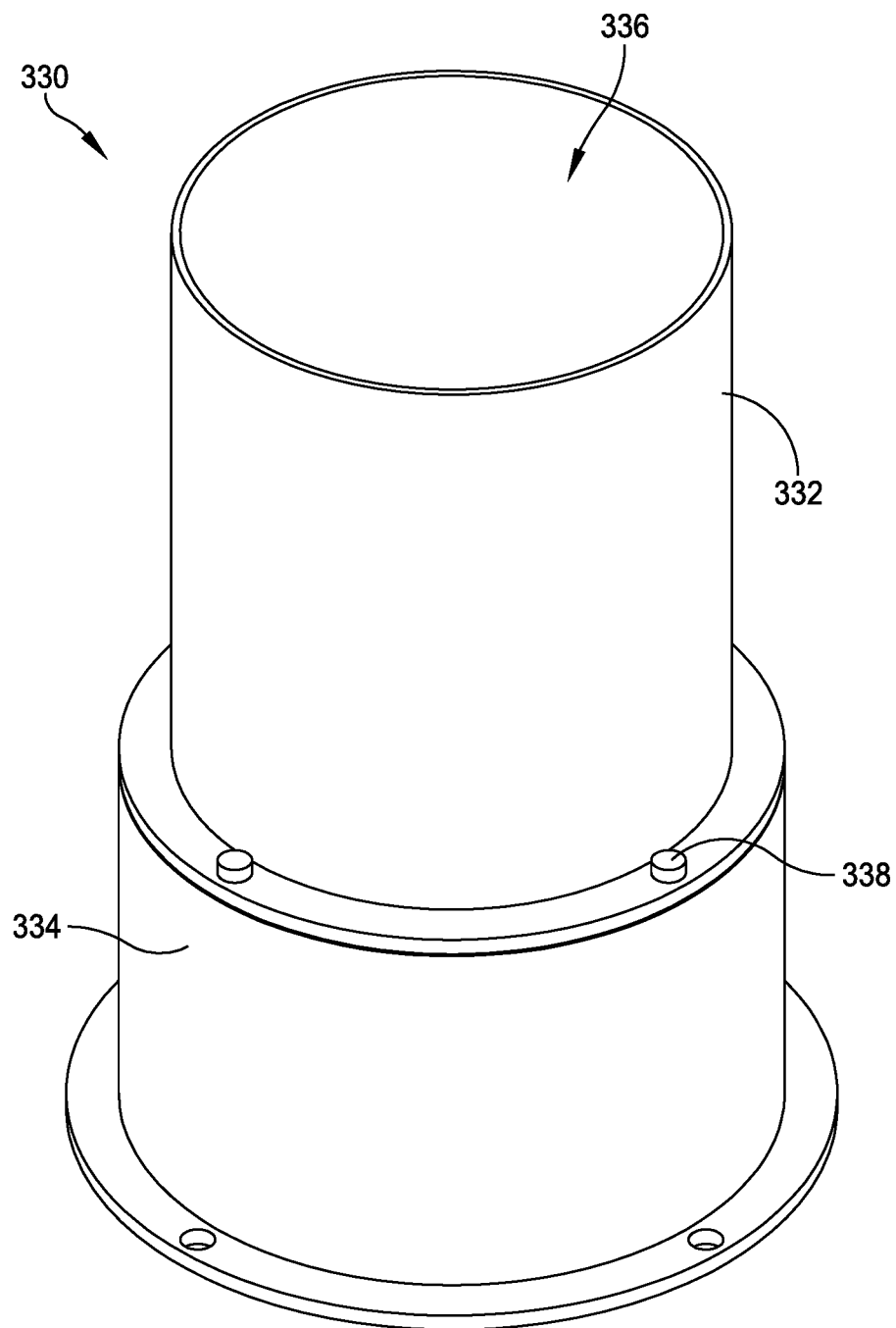
FIGS. 4A-4D illustrate perspective, exploded, side, and cross-sectional views of another embodiment of a cannister assembly for incorporation into the mixing assembly of FIG. 2.
Figure 4B:
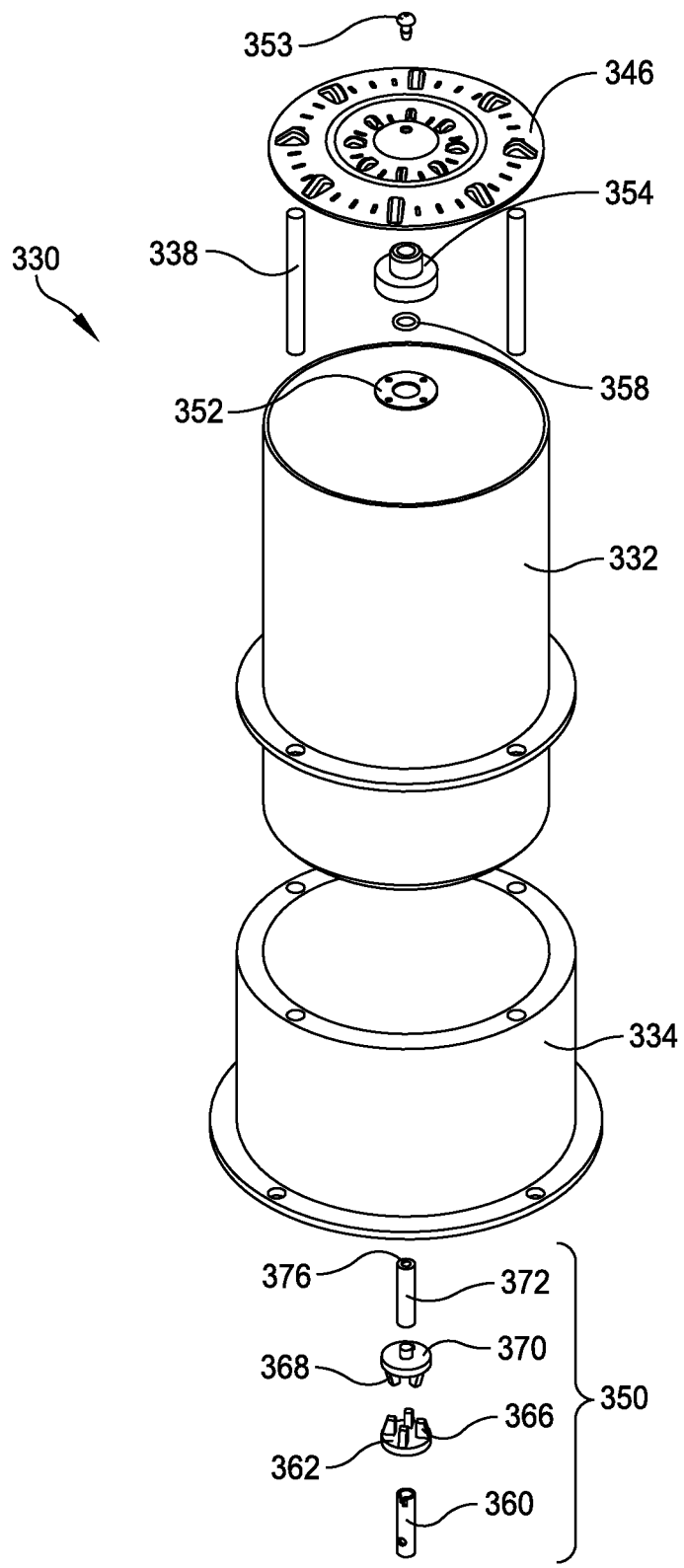
Figure 4C:
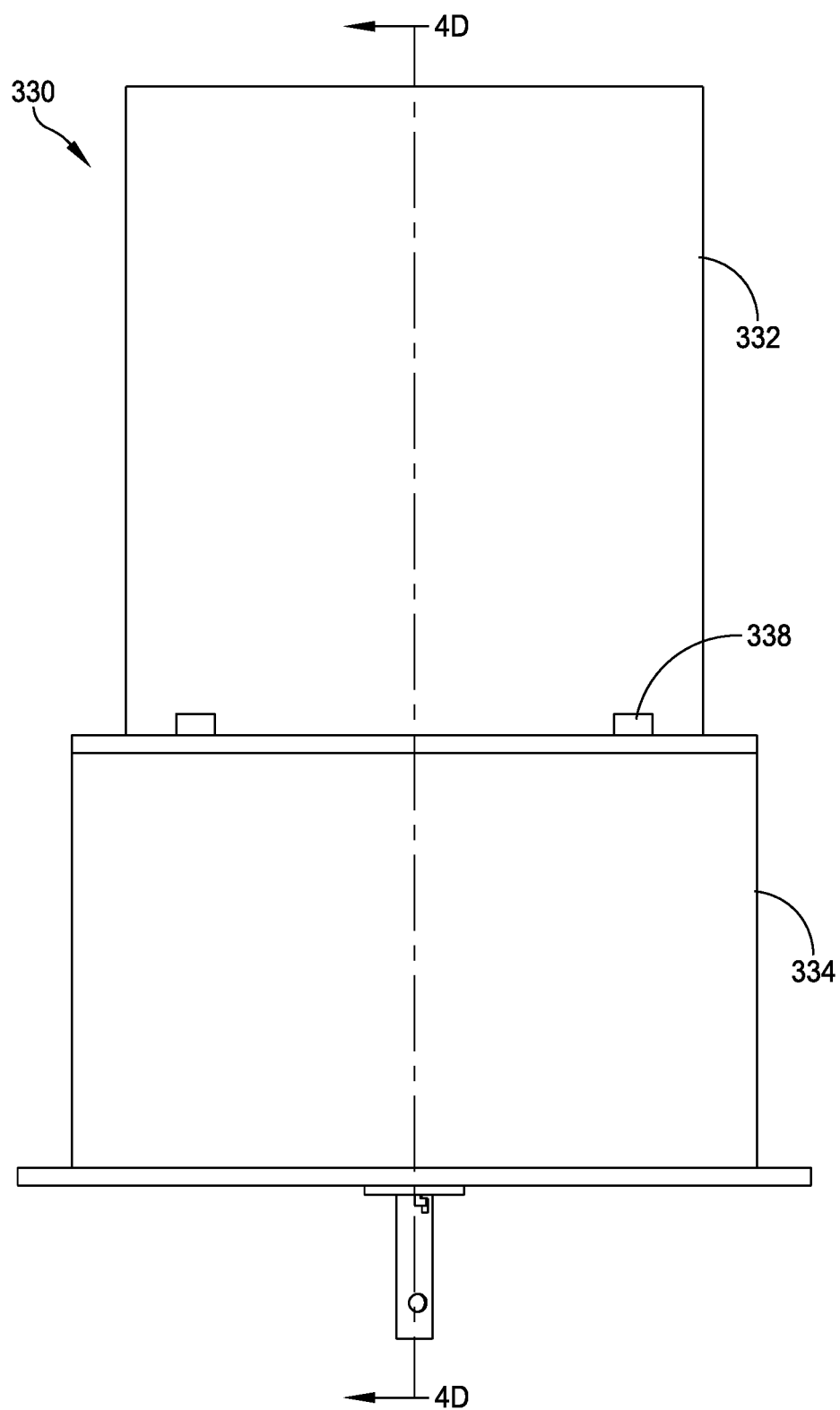
Figure 4D:
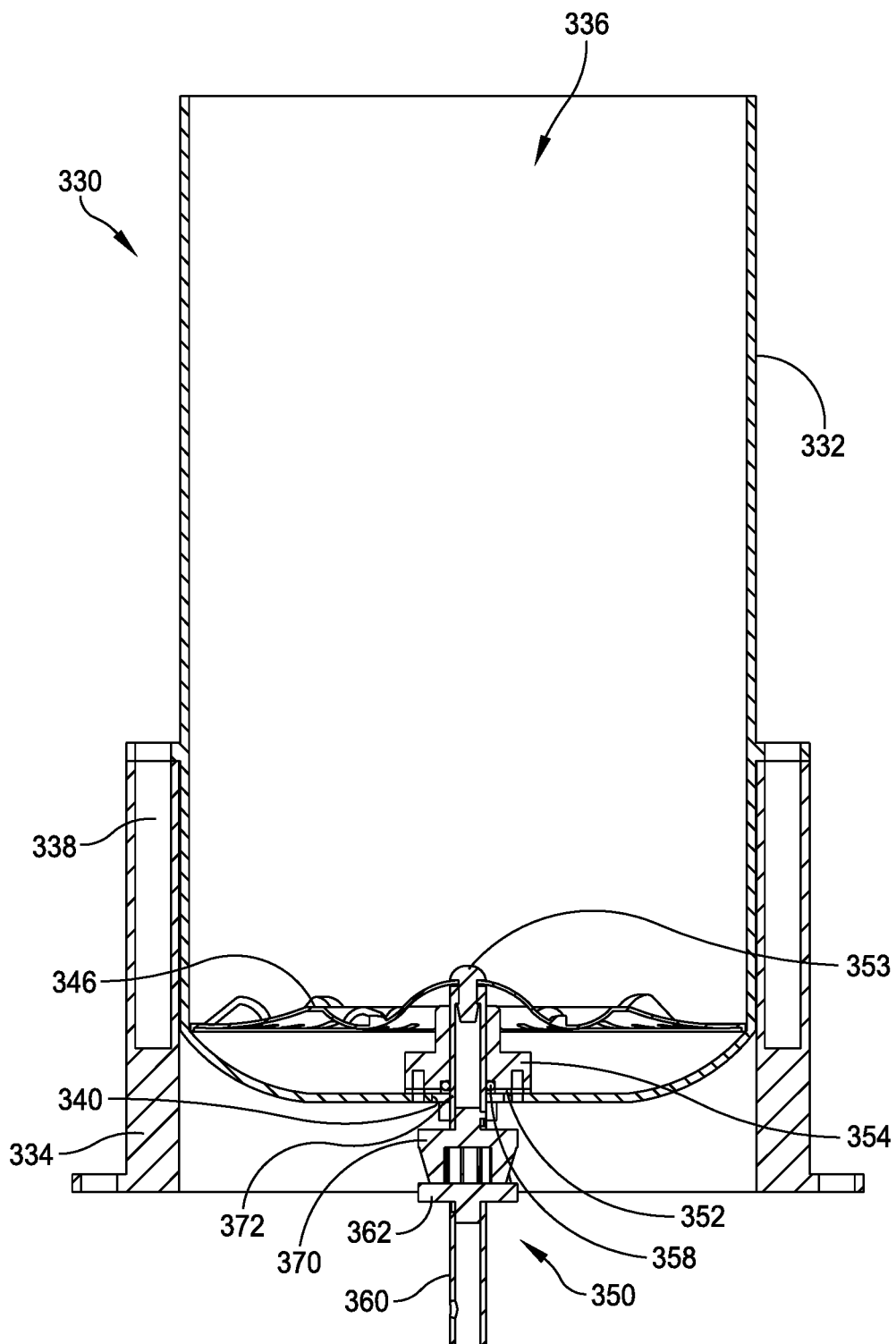

To prevent undesirable leakage during operation, a large o-ring 254 may form a seal between the drainable base 234 and an outer perimeter 256 of the agitator 246, and a small o-ring 258 may form a seal between a top end of the rotation access protrusion 240 and the agitator 246, as shown in the exploded and cross-sectional views of FIGS. 3B and 3D, respectively.

One embodiment of the rotation translation assembly 250 may include a motor pivot 260 that is directly or indirectly coupled with the motor 450 in any appropriate manner. In one embodiment, the motor pivot 260 may be coupled with an output shaft of the motor 450 via a drive coupling. In another embodiment, the motor pivot 260 may be disposed upon the wheel 416 that is fitted with the motor-driven belt 417, as discussed above in relation to FIG. 2.

The rotation translation assembly 250 may further include a lower clutch 262 affixed to a top surface of the motor pivot 260 via any appropriate attachment mechanism including, for example, a set screw 264. The lower clutch 262 may include a plurality of lower protrusions 266 that are configured to enmesh with a corresponding plurality of upper protrusions 268 of a mated upper clutch 270, which is, in turn, affixed to a drive pivot 272 via any appropriate fastener such as, for example, a set screw 274.

An upper end 276 of the drive pivot 272 may extend through the rotation access protrusion 240 formed within the drainable base 234, where it attaches to the agitator 246 via the screw 252, discussed above. Another small o-ring 258 may encircle the drive pivot 272 along a seam where the pivot 272 enters the rotation access protrusion 240 for further leak prevention, as shown in FIGS. 3B and 3D.

In operation, the motor 450 may directly or indirectly rotate the motor pivot 260. That rotational motion is transferred from the lower protrusions 266 of the lower clutch 262 to the upper protrusions 268 of the mated upper clutch 270 and, in turn, to the attached drive pivot 272 and agitator 246, such that reagent liquid contained within the mixing chamber 236 is agitated by the agitator 246 within the mixing chamber 236, while the mated cannister chamber body 232 and drainable base 234 remain stationary and stabilized by the housing 400 and frame 402.

Embodiments of this internally agitated cannister assembly 230 provide an elegant solution with a minimal number of interacting and/or threaded components to provide for easy assembly and disassembly for use and later sterilization within the clean room environment.

FIGS. 4A-4D illustrate perspective, exploded, side, and cross-sectional views of another embodiment of a cannister assembly 330 for use in the mixing sub-assembly 120. The cannister assembly 330 is similar to the cannister assembly 230 in that the assembly's agitation is initiated via a spinning agitator 346 positioned at a bottom of a mixing chamber 336, while a mated cannister chamber body 332 and base 334 remain stationary within the stabilizing housing 400 and frame 402.

In this embodiment, the cannister chamber body 336 may be aligned with and pinned to the base 334 via a plurality of locating pins 338. A bottom of the cannister chamber body 332 may include an access aperture 340 configured to receive a rotation translation assembly 350, which may include a motor pivot 360, a lower clutch 362 having a plurality of lower protrusions 366, a mated upper clutch 370 having a plurality of upper protrusions 368 that enmesh with the plurality of lower protrusions 366, and a drive pivot 372. The components of the rotation translation assembly 350 may couple in any appropriate manner using any appropriate mechanism. For example, the motor and drive pivots 360, 372 and the lower and upper clutches 362, 370, respectively, may be keyed or notched such that they self-interlock or interconnect, rather than being connected via fasteners.

Within the mixing chamber 336, a stack including a gasket 352, a small o-ring 358, and a pivot cover 354 may align about and above the access aperture 340 formed in the cannister chamber body 332. The drive pivot 372 may protrude from below, through an open bottom portion of the base 334, through the access aperture 350 in the cannister chamber body 332, and through the gasket 352, o-ring 358, and pivot cover 354, where the agitator 346 may be affixed to an upper end 376 of the drive pivot 372 via a plug 353.

In this embodiment, reagent within the mixing chamber 336 may be drained via the access aperture 350 after removal of the plug 353 or the rotation translation assembly 350. Alternatively, a bottom of the cannister chamber body 332 may incorporate an outlet (not shown) for tube drainage from the mixing chamber 336 between mixing cycles.

Similar to the cannister assembly 230, discussed above in relation to FIGS. 3A-3D, the motor 450 may directly or indirectly rotate the motor pivot 360. This rotational motion is transferred between the protrusions 366, 368 of the mated upper and lower clutches 362, 370 to the drive pivot 372 and the affixed agitator 246, such that reagent liquid contained within the mixing chamber 336 is agitated by the agitator 346 within the mixing chamber 336, while the mated cannister chamber body 332 and the base 334 remain stationary and stabilized by the housing 400 and frame 402.

All of the tissue-contacting components of the assemblies discussed herein, including, for example, embodiments of the cannister chamber body, the base, the agitator, the pivots, the clutches, and so on, may be formed of stainless steel so that they may be steam sterilized (e.g., sterilized via autoclave), and components may be welded to one another or to the frame 402 for added structural support. In some embodiments, components such as the o-rings may be formed of biocompatible materials (e.g., plastics) that can withstand repeated steam sterilization cycles. Threading and screws are minimized to reduce and/or eliminate areas vulnerable to contamination. The tubing 140 may be sterilizable prior to use and discarded after each use. In one embodiment, the cannister assembly may be a single-use assembly that is disposed of after each use.

Notably, one skilled in the art will understand that system components may be altered and may take any appropriate size, shape, type, and/or configuration. For example, embodiments of the cannister assembly 130, 230, 330 may vary in dimensions and may be driven on a horizontal, rather than vertical, axis. Any appropriate number of reagents and reagent containers may be incorporated into the system, and any appropriate type and/or models of components may be used for, for example, the pinch valves, rotary unions, motor(s), pump(s), and so on. Notably, while embodiments of the cannister assembly 230, 330 employ agitators 246, 346 located at the bottom portions of the mixing chambers 232, 332, the agitator or impeller may be located at any appropriate location within the mixing chamber 236, 336 that enables agitation of the reagent fluids contained therein, including at the bottom, the side, or the top of the mixing chamber. Further, one or more agitators may be employed to agitate the reagent fluids. In addition, the mesh bag 142 or another net or mesh barrier may be employed within embodiments of the externally or internally agitated cannister assemblies 130, 230, 330 to prevent bone or tissue fragments from falling onto the agitator and/or otherwise interfering with agitation and/or drainage. Moreover, flow sensors may be added to measure flow into the reagent inlet to increase the accuracy of reagent readings.

Returning to FIG. 1 and as discussed above, the mixing assembly 110 may be communicatively coupled with a control and reporting system 500 configured to communicate with and control the mixing assembly 110 and report on process or job information and/or statistics. In some embodiments, the control and reporting system 500 may include a communication system 504 that provides communication abilities to the control and reporting system 500. To that end, the communication system 504 may include one or more analog switches, servers, IP gateways, PBX systems, etc. For example, in some embodiments, the communication system may be operable to provide communications through a network 510, which may include, for example, the Internet. Additionally or alternatively, the network may include a wireless cellular network, a local area network (LAN), or the like. In one embodiment, the communication system 504 may be directly wired to other system components via one or more digital input/output terminals.

The control and reporting system 500 may also include one or more processors 506, as well as data storage/memory 508 (volatile and non-volatile memory), which may be configured to store software modules as well as job data or information including, for example, tissue-type information, procedure cycle information, donor numbers, tissue weights, job numbers, and so on.

In one embodiment, the communication system 504, the processor(s) 506, and the data storage 508 may be provided via a single-board computer (SBC) or microcontroller 502 such as, for example, a Raspberry Pi single-board computer. In other embodiments, the communication system 504, processor(s) 506, and data storage 508 may be separate, linked components. These components, or sub-components thereof, may be combined or distributed in any appropriate manner across a single or multiple locations and/or distributed computing platforms.

To enable the control and reporting system 500 to communicate via the communication system 504 and the network 510, the operator or technician may operate a user terminal 512 configured to securely compile and transmit the demineralization or decellularization job information to and from other system components. The user terminal 512 may be any appropriate user device such as, for example, a desktop computer, laptop computer, tablet computer, smartphone, or the like. In some embodiments, the user terminal 512 may be a specialized terminal configured specifically for the automated system for tissue demineralization.

Figure 5:
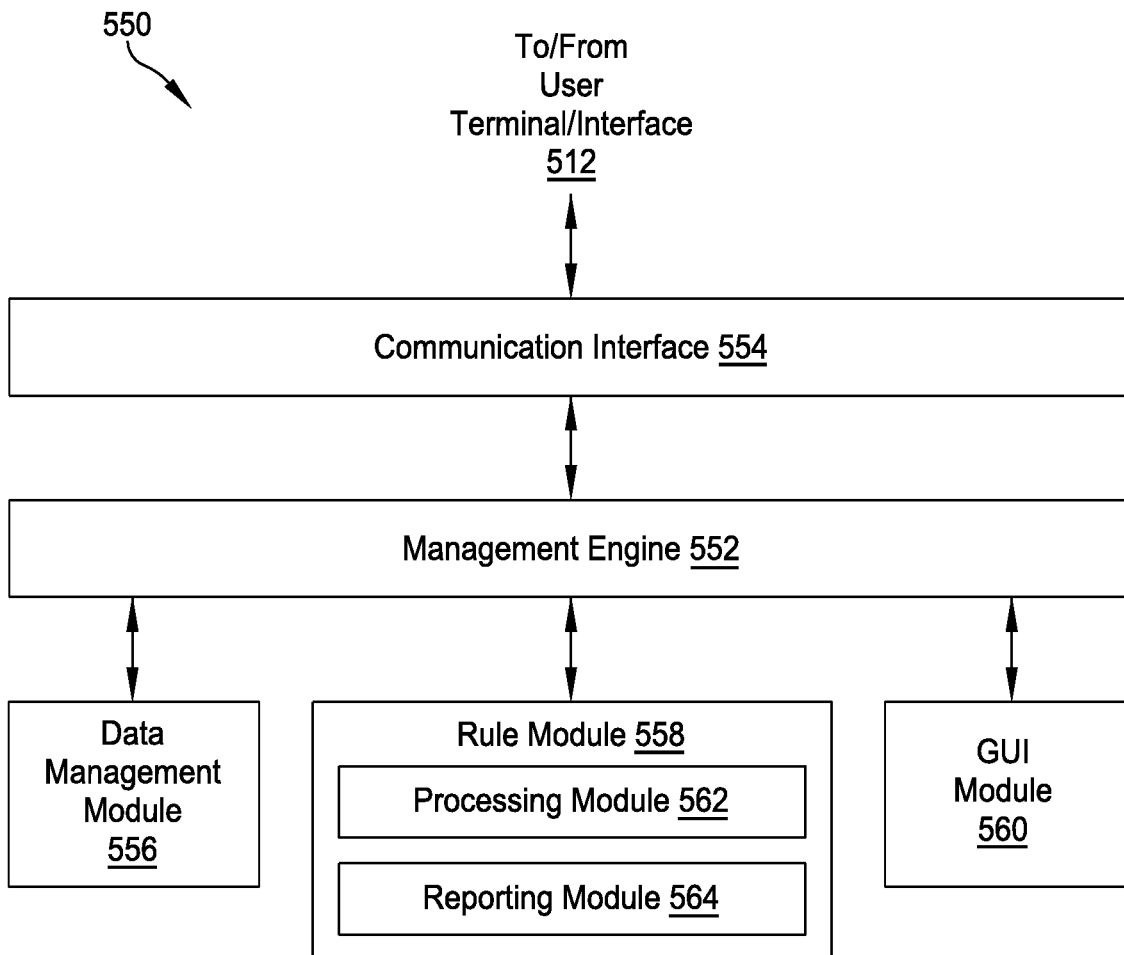
FIG. 5 provides a block diagram depicting illustrative demineralization and decellularization process and reporting software according to some embodiments.

FIG. 5 provides a block diagram depicting illustrative demineralization and decellularization process and reporting software 550 according to some embodiments. In various implementations, such software 550 may be executed by the processors 506 of the control and reporting system 500 (e.g., the microprocessors of the microcontroller). As shown, a management engine 552 may be coupled to a communication interface 554, a data management module 556, a rule module 558, and a graphical user interface (GUI) module 560. The management engine 552 may communicate with the user terminal 512 via the communication interface 554. The management engine 552 may be configured to perform a variety of demineralization and/or decellularization processes and reporting operations including those described below with respect to FIG. 6.

The communication interface 554 may enable the demineralization and decellularization process and reporting software 550 to exchange information with other systems and/or system components, including the user terminal 512 and the mixing assembly 110 and sub-assembly 120 via the network 510 or via the directly wired connections. In some embodiments, the communication interface may be configured to transmit and/or receive information using secure socket layer (SSL) encryption. Additionally or alternatively, other connections may also be used, such as, for example, XML file transmission utilizing file transfer protocol (FTP), hypertext transfer protocol (HTTP) POST transactions, or other data transmission protocols. The communication interface 554 may further include any of a variety of standardized application programming interfaces (APIs) configured to allow different software programs to communicate (e.g., to request services and to respond to such requests) in an autonomous, web-based, and/or platform-independent manner. For example, the control and reporting system 500 may choose to reveal job processing data to an external program such as, for example, an Excel spreadsheet. The communication interface may access the exposed data and/or functions via the appropriate API(s).

The data management module 556 may include any suitable database management system (DBMS) or applications configured to manage the creation, maintenance, and use of data stored in the storage 508 of FIG. 1. The rule module 558 may include one or more sets of rules, in any suitable format, that provide a framework for demineralization and/or decellularization process management and reporting of the process data, as described in further detail below. For example, the rule module may include a processing module 562 that incorporates predefined demineralization and decellularization procedures to be carried out by the mixing assembly 110 according to required and/or accepted allograft processing procedures (e.g., number of reagents, timing of mixing cycles, etc.). The rule module 558 may also include a reporting module 564 including instructions for reporting information, including job processing information, to the user terminal and/or, for example, an Excel spreadsheet or another external record-keeping program.

The GUI module 560 may be configured to provide, for example, a web-based user interface (WUI) that implements JAVA®, AJAX®, ADOBE FLEX®, MICROSOFT.NET®, or similar technologies to provide real-time user control (e.g., touchscreen control on the user terminal). In other embodiments, the GUI module 560 may implement a command line interface, an application interface, or another suitable interface using non-web-based technologies.

In various embodiments, a GUI 566 may be displayed to a user at the user terminal 512 of FIG. 1 via the GUI module 560 of FIG. 5. The GUI 566 may be operable to display information and/or receive commands from the user at the user terminal 512. In various implementations, the GUI 566 may be displayed, via a number of appropriate preconfigured and interactive screens $568_{1-n}$, to the user at the user terminal 512 via the communication interface 554 and the network 510. For example, the GUI module 560 may display one or more preconfigured screens $568_{1-n}$ at the user terminal 512 that guide the user in entering job information, parameters, and/or constraints. Further, job processing information may be reported and displayed via the GUI module 560 upon one or more of the interactive preconfigured screens $568_{1-n}$ displayed at the user terminal 512.

A browser or application window (not shown) on the user terminal may be configured to display text content, image content, input features, navigable links, etc. of the preconfigured screens $568_{1-n}$ of the GUI 566. Each preconfigured screen $568_{1-n}$ may include any appropriate type of content in various combinations, and the screen(s) displayed to the users may be specific to the viewing platform. For example, the screen(s) presented at the user terminal 512 may be tailored based on a variety of factors including, for example, the type of information to be collected, transmitted, presented, or reported, security concerns, user permissions, the type and/or size of the terminal 512, and so on.

GUI screen content may be interspersed or combined in any suitable fashion according to the capabilities of the browser or application and language used to implement the GUI 566, and may be displayed in any suitable area of the browser or application window. In some embodiments, the window may be generated and managed by a web browser such as, for example, MICROSOFT EXPLORER®, FIREFOX®, SAFARI®, CHROME®, etc., implemented by the control and reporting system 500.

In various embodiments, the modules shown in FIG. 5 may represent sets of software routines, logic functions, and/or data structures that are configured to perform specified operations. Although these modules are shown as distinct logical blocks, in other embodiments, at least some of the functionality provided by these modules may be combined into fewer blocks or parceled into additional blocks. Conversely, any given one of the modules may be implemented such that its functionality is divided among two or more logical blocks. Moreover, although shown with a particular configuration, in other embodiments these various modules may be rearranged in other suitable ways.

The various systems shown in FIGS. 1-5 may allow the execution of procedures relating to the demineralization of bone portions, the decellularization of soft tissue portions, and/or the demineralization or decellularization of other appropriate tissue types. Generally speaking, such methods may include information collection, demineralization/decellularization procedure management, and/or job or process reporting.

Figure 6:
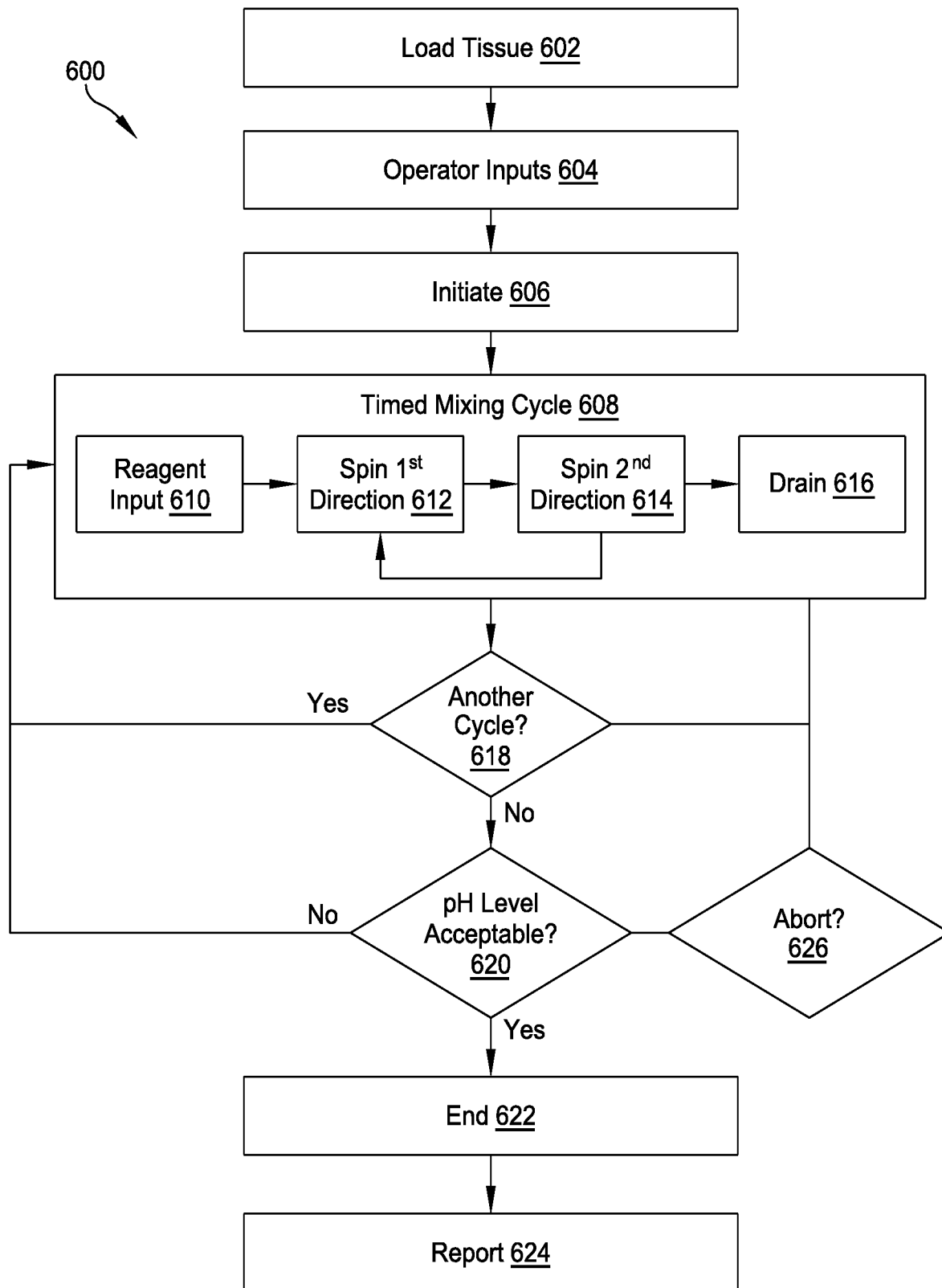
FIG. 6 provides a flowchart depicting an exemplary method for managing an automated demineralization or decellularization process using embodiments of the automated system of FIG. 1.

FIG. 6 provides a flowchart depicting an exemplary method (600) for managing an automated demineralization or decellularization process. The method (600) begins when the operator loads the tissue portion (e.g., ground cortical or cancellous bone or soft tissue) into the mixing chamber (602). In one embodiment, the tissue may be loaded into the mesh bag 142 and then loaded into the mixing chamber 136, 236, 336. Once loaded, the operator may input relevant procedure information into the appropriate preconfigured screens $568_{1-n}$ of the GUI 566 displayed at the user terminal 512 (604). Such information may include, for example, donor information such as a donor number, a tissue type or weight, a job number, and/or a process protocol identifier. Once the operator inputs are complete (604), the demineralization or decellularization process is initiated (606) and the mixing assembly 110 begins an automated progression through each stage of the demineralization or decellularization process, beginning with a first timed mixing cycle (608) in which a defined quantity of a first reagent is input into the mixing chamber (610). In this embodiment, the first quantity of the first reagent may be 4 liters of hydrochloric acid. Once all of the first reagent is pumped into the mixing chamber (610), the motor spins the agitator 246, 346 in a first direction for a specified period of time (e.g., 15 seconds to 5 minutes) (612), and then reverses and spins the agitator in a second direction for a specified period of time (e.g., 15 seconds to 5 minutes) (614), repeating the first and second direction spinning agitation for a specified duration appropriate for the specific demineralization or decellularization procedure (e.g., 5 to 60 minutes). Changing the spinning directions stops the formation of a vortex, which causes the tissue to become "trapped," and ensures that the reagent fully penetrates the tissue.

Once the spinning agitation is complete, the pinch valve on the reagent outlet is opened, and the reagent is allowed to drain into the waste container via gravity (616). The timed mixing cycle (608) may then be repeated for each reagent to be mixed with the tissue portion (618). For example, the timed mixing cycle may be repeated for an additional cycle of the first reagent, for a second reagent (e.g., 2 liters of water), for a third reagent (e.g., 2 liters of phosphate buffered saline (PBS)), and for a repeat of the second reagent (e.g., a final water wash).

After all requisite reagent cycles (608) have been completed, including the final water wash, the pH meter 139 located at the reagent outlet may be read for the final water wash draining into the waste container (620). If the pH level is not acceptable (e.g., is not at least 6.0), then the PBS and the final water washes may be repeated until the pH level is acceptable. Once the demineralization or decellularization process is complete (622), the GUI 566 on the user terminal 512 may display that the process has ended via one or more of the preconfigured screens $568_{1-n}$ and report the details of the process (e.g., report the details of each timed mixing cycle—reagent type, timing, repetition, etc.) (624). In one embodiment, the report may be output to an Excel spreadsheet. Throughout the process, the GUI on the user terminal may display which cycle is in progress as well as an elapsed and a remaining time, both for the particular cycle and for the process as a whole. At any point during the process, the operator may use the GUI 566 of the user terminal to abort the process (626).

The following protocol summarizes an exemplary protocol for bone demineralization using embodiments of the automated system for tissue demineralization 100 and the tissue processing method (600) discussed above in relation to FIG. 6: (1) Place a 1200-1400 g portion of ground cortical or cancellous bone into the mesh bag 142 and load the bag 142 into the mixing chamber 236, 336; (2) Provide operator inputs regarding the tissue type, donor info, demineralization process requirements or identifier, etc.; (3) Initiate the mixing assembly 110; (4) Pump 1-4 liters of 0.5N-2N HCl (depending on tissue weight) into the mixing chamber; (5) Run a first timed agitation cycle for 20-75 minutes, including spinning the agitator 246, 346 in a first direction for 15 seconds to 5 minutes, spinning the agitator 246, 346 in a second, opposite direction for 15 seconds to 5 minutes, and repeating through the requisite agitation time; (6) Drain the mixing chamber; (7) Repeat steps (4)-(6) until all requisite timed reagent mixing cycles are complete; (8) Pump 1-4 liters of sterile water into the mixing chamber; (9) Run a timed water mixing cycle for 5 to 60 minutes, including spinning the agitator in the first direction for 15 seconds to 5 minutes, spinning the agitator in the second, opposite direction for 15 seconds to 5 minutes, and repeating through the requisite water agitation time; (10) Drain the mixing chamber; (11) Pump 1-4 liters of sodium phosphate buffer into the mixing chamber; (12) Run a timed sodium phosphate buffer mixing cycle for 5 to 60 minutes, including spinning the agitator in the first direction for 15 seconds to 5 minutes, spinning the agitator in the second, opposite direction for 15 seconds to 5 minutes, and repeating through the requisite sodium phosphate buffer agitation time; (13) drain the mixing chamber; (14) Pump 1-4 liters of sterile water into the mixing chamber; (15) Run a timed water mixing cycle for 5 to 60 minutes, including spinning the agitator in the first direction for 15 seconds to 5 minutes, spinning the agitator in the second, opposite direction for 15 seconds to 5 minutes, and repeating through the requisite water agitation time; (16) drain the mixing chamber; (17) test the pH level; (18) if the pH level is not greater than or equal to 6.0, repeat steps 11-17 until the proper pH level is achieved; and (18) if the pH level is greater than or equal to 6.0, end the process and report.

The following protocol summarizes an exemplary protocol for soft tissue decellularization employing embodiments of the automated system for tissue demineralization 100 and the tissue processing method (600) discussed above in relation to FIG. 6. The decellularization protocol is suitable for full thickness skin, partial thickness skin, tendon, or other soft tissues. The protocol steps include: (1) Place the tissue into the mesh bag 142 and load the bag 142 into the mixing chamber 236, 336, planning for a final tissue to reagent fluid ratio of 200 g of tissue to 2 liters of fluid within the mixing chamber; (2) Provide operator inputs regarding the tissue type, donor info, decellularization process requirements, protocol selection, etc.; (3) Initiate the mixing assembly 110; (4) Pump 1-4 liters of decellularizing solution (depending on tissue weight) into the mixing chamber, where the decellularizing solution is any known decellularization solution such as those outlined in Gilpin and Yang. "Decellularization Strategies for Regenerative Medicine: From Processing Techniques to Applications." Biomed Res Int. v2017 (2017). Web. 20 Apr. 2017., preferring non-enzymatic solutions such as, for example, 0.25% w/w-0.50% w/w Sodium Dodecyl Sulfate (SDS); (5) Run a first timed agitation cycle for 20-75 minutes, including spinning the agitator 246, 346 in a first direction for 15 seconds to 5 minutes, spinning the agitator 246, 346 in a second, opposite direction for 15 seconds to 5 minutes, and repeating through the requisite agitation time; (6) Drain the mixing chamber; (7) Repeat steps (4)-(6) until all requisite timed reagent mixing cycles are complete; (8) Pump 1-4 liters of sterile water into the mixing chamber; (9) Run a timed water mixing cycle for 5 to 60 minutes, including spinning the agitator in the first direction for 15 seconds to 5 minutes, spinning the agitator in the second opposite direction for 15 seconds to 5 minutes, and repeating through the requisite water agitation time; (10) Drain the mixing chamber; (11) Pump 1-4 liters of sodium phosphate buffer into the mixing chamber; (12) Run a timed sodium phosphate buffer mixing cycle for 5 to 60 minutes, including spinning the agitator in the first direction for 15 seconds to 5 minutes, spinning the agitator in the second, opposite direction for 15 seconds to 5 minutes, and repeating through the requisite sodium phosphate buffer agitation time; (13) drain the mixing chamber; (14) Pump 1-4 liters of sterile water into the mixing chamber; (15) Run a timed water mixing cycle for 5 to 60 minutes, including spinning the agitator in the first direction for 15 seconds to 5 minutes, spinning the agitator in the second, opposite direction for 15 seconds to 5 minutes, and repeating through the requisite water agitation time; (16) Drain the mixing chamber; (17) test the pH level; (18) if the pH level is not greater than or equal to 6.0, repeat steps 11-17 until the proper pH level is achieved; and (18) if the pH level is greater than or equal to 6.0, end the process and report.

The system and methods described above speak to the process of demineralization of bone and decellularization of skin, tendon, and other allograft tissues. In these embodiments, for example, the number of reagents may be increased from three to seven to include NaOH, HCL NaHCO$_3$, Microcyn, PBS, water, and hydrogen peroxide. The automated system and methods may similarly by used in any appropriate manner of tissue processing that requires mixing human tissue with one or more reagents.

Embodiments of the automated system and exemplary tissue processing method discussed above allow an operator to load the tissue portion into the mixing chamber, input process information, begin the processing cycle, and then leave while the tissue processes. At the end of the process, cycle information is conveniently reported so that the operator may confirm that a successful process, including a proper pH level, has completed. The system and associated methods of use remove human error from the bone and tissue demineralization and decellularization processes, ensuring that the tissue portion is mixed with the correct reagents, in the correct amounts, for the exact required agitation time periods for each progressive reagent mixing cycle. In addition, because the operator does not need to manually transition between mixing cycles, the operator is free to perform other duties and multi-task while the process progresses. If there is an error, the error is reported at the completion of the process, enabling the operator to take appropriate action. Moreover, embodiments of the system and methods described herein allow for the processing of a quantity of bone that equals a "whole body" allotment of donor-derived bone (e.g., 1200-1400 grams). Thus, the "whole body" of a single donor may be processed before the mixing subassembly 120 is dismantled for sterilization, reducing the operator's cleanup obligation, further increasing efficiency and productivity, and reducing the amount of reagent required for processing.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. An automated tissue processing system for conducting an automated demineralization or decellularization process upon a tissue portion, comprising:
   a mixing assembly, including:
      a cannister forming a mixing chamber, a reagent inlet configured to convey an entire volume of a reagent into the mixing chamber, and a reagent outlet configured to selectively drain the entire volume of the reagent from the mixing chamber at a completion of a mixing cycle;
      an agitator disposed within the mixing chamber;
      a barrier disposed within the mixing chamber, the barrier having a configuration to prevent the tissue portion disposed in the mixing chamber from contacting the agitator;
      a motor operably coupled with the agitator, the motor configured to selectively revolve the agitator in a first direction and in a second direction relative to the cannister;
      at least one pump configured to inject a measured quantity of each of a first, a second, and a third reagent into the reagent inlet; and
      a pH meter disposed adjacent to the reagent outlet and configured to measure a pH level of the first, the second, and the third reagents draining from the reagent outlet at the completion of the mixing cycle; and
   a control and reporting system in communication with the mixing assembly, the control and reporting system including:
      a data storage storing a processing module and a reporting module;
      a processor executing the processing and the reporting modules; and
      a graphical user interface implemented by the processor and displayed upon a user terminal, the graphical user interface having a number of interactive and preconfigured screens that enable a user to control the mixing assembly to complete the automated demineralization or decellularization process upon the tissue portion placed within the mixing chamber;
   wherein the control and reporting system is configured to operate the mixing assembly in an automated configuration to provide a discrete iteration of the mixing cycle for each one of the first, the second, and the third reagents, and the mixing cycle in the discrete iteration includes (1) conveying the entire volume of the first, the second or the third reagent into the mixing chamber, (2) revolving the agitator, and (3) selectively draining the entire volume of the respective first or second or third reagent from the mixing chamber at the completion of the mixing cycle.

2. The automated tissue processing system of claim 1, wherein the tissue portion comprises a bone portion or a soft tissue portion.

3. The automated tissue processing system of claim 1, wherein the at least one pump is further configured to inject measured quantities of each of a fourth, a fifth, a sixth, and a seventh reagent.

4. The automated tissue processing system of claim 1, wherein the at least one pump comprises three discrete pumps, each operably coupled with the reagent inlet.

5. The automated tissue processing system of claim 1, wherein the at least one pump comprises a multichannel pump.

6. The automated tissue processing system of claim 1, wherein the agitator is disposed adjacent to a bottom of the mixing chamber.

7. The automated tissue processing system of claim 1, wherein the barrier includes a mesh material.

8. The automated tissue processing system of claim 7, wherein the mesh material is configured to anchor to the canister.

9. The automated tissue processing system of claim 1, wherein the barrier is a mesh bag.

10. The automated tissue processing system of claim 9, wherein the mesh bag is configured to anchor to the canister.

11. The automated tissue processing system of claim 1, wherein the barrier is a net.

12. The automated tissue processing system of claim 11, wherein the net is configured to anchor to the canister.

* * * * *